United States Patent
Tsudera et al.

(10) Patent No.: US 7,179,931 B2
(45) Date of Patent: Feb. 20, 2007

(54) HIGH-PURITY TRIMETHYLALUMINUM AND PURIFICATION METHOD OF CRUDE TRIMETHYLALUMINUM

(75) Inventors: Takanobu Tsudera, Joetsu (JP); Shuji Tanaka, Joetsu (JP); Daisuke Iwai, Joetsu (JP); Hiromi Nishiwaki, Joetsu (JP); Takayuki Honma, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/154,535

(22) Filed: Jun. 17, 2005

(65) Prior Publication Data

US 2005/0283016 A1    Dec. 22, 2005

(30) Foreign Application Priority Data

Jun. 18, 2004   (JP) .............................. 2004-181009

(51) Int. Cl.
*C07F 5/06* (2006.01)

(52) U.S. Cl. ...................................... 556/187
(58) Field of Classification Search ................ 556/187
See application file for complete search history.

(56) References Cited

U.S. PATENT DOCUMENTS

| 4,650,895 A | * | 3/1987 | Kadokura et al. ........... 556/182 |
| 4,720,561 A | | 1/1988 | Bradley et al. |
| 4,797,500 A | | 1/1989 | Kadokura et al. |
| 4,847,399 A | * | 7/1989 | Hallock et al. ................. 556/1 |
| 5,288,885 A | * | 2/1994 | Smit et al. ...................... 556/1 |
| 5,455,364 A | | 10/1995 | Yako et al. |
| 6,482,968 B1 | * | 11/2002 | Tran et al. .................... 556/187 |

FOREIGN PATENT DOCUMENTS

| GB | 2 183 651 A | | 6/1987 |
| GB | 2183651 A | * | 6/1987 |
| JP | 62-132888 | | 6/1987 |
| JP | 5-35154 | | 5/1993 |
| JP | 7-224071 | | 8/1995 |
| JP | 8-12678 | | 1/1996 |

OTHER PUBLICATIONS

Hata et al., Residual Impurities in Epitaxial Layers Grown by MOVPE, Journal of Crystal Growth, vol. 93, No. 1-4, pp. 543-549 (1988).*
Pasynkiewicz et al., Journal of Organometallic Chemistry, vol. 25, pp. 29-32 (1970).*
S. Pasynkiewicz et al. "Synthesis of Trimethylaluminum", J. Organomental Chem, 25(1970), pp. 29-32, XP-002353845.
European Search Report dated Nov. 14, 2005, issued in corresponding European Application No. 05 253800.

* cited by examiner

*Primary Examiner*—Porfirio Nazario-Gonzalez
(74) *Attorney, Agent, or Firm*—Westerman, Hattori, Daniels & Adrian, LLP.

(57) ABSTRACT

High-purity trimethylaluminum has the following impurity contents: organosilicon components $\leq 0.5$ ppm, chlorine components $\leq 20$ ppm, hydrocarbon components $\leq 1,000$ ppm, $Ca \leq 0.05$ ppm, $Fe \leq 0.05$ ppm, $Mg \leq 0.05$ ppm, $Na \leq 0.05$ ppm, Si (Si components other than the organosilicon components) $\leq 0.07$ ppm, $Zn \leq 0.05$ ppm, and $S \leq 0.05$ ppm. The high-purity trimethylaluminum can be obtained by removing impurities from crude trimethylaluminum through distillation and evaporation.

5 Claims, No Drawings

HIGH-PURITY TRIMETHYLALUMINUM AND PURIFICATION METHOD OF CRUDE TRIMETHYLALUMINUM

CROSS-REFERENCE TO RELATED APPLICATION

This non-provisional application claims priority under 35 U.S.C. §119(a) on Patent Application No. 2004-181009 filed in Japan on Jun. 18, 2004, the entire contents of which are hereby incorporated by reference.

BACKGROUND OF THE INVENTION

This invention relates to high-purity trimethylaluminum, and also to a purification method of crude trimethylaluminum.

Compound semiconductor materials have uses in the electronics industry in such applications as microwave oscillators, semiconductor light-emitting diodes, lasers and infrared detectors. The quality of a compound semiconductor available from an epitaxial growth of an organometallic compound is significantly controlled by impurities, especially those in the organometallic compound as a raw material. Therefore, high purity is required for the organometallic compound to obtain the compound semiconductor material with a high function.

The impurities in an organometallic compound, especially in trimethylaluminum, include hydrocarbon components, organosilicon components, alkylaluminum oxides, metal compounds, etc. Among these impurities, organosilicon components and alkylaluminum oxides generally have higher or similar vapor pressures compared with trimethylaluminum so that they may form silicon inclusions and oxygen inclusions in a compound semiconductor to be produced from trimethylaluminum, and therefore, are considered to be particularly harmful.

Further, the metal compounds are also considered to be compounds having higher or similar vapor pressures compared with trimethylaluminum, such as titanium compounds, zinc compounds, and sulfur compounds.

The alkylaluminum oxides, on the other hand, are considered to be included or formed during the synthesis and handling operations of trimethylaluminum, and are regarded as one of factors that deteriorate the qualities of compound semiconductors.

As a conventional purification process of crude trimethylaluminum, the distillation process is widely known. With simple batchwise distillation or continuous distillation, however, it is difficult to remove organosilicon components or alkylaluminum oxides, because the inclusion of such impurities are considered to be attributable to the production process, production facilities and process operations of crude trimethylaluminum as a raw material.

Known production processes of trimethylaluminum may be divided roughly into the following three types of processes:

(1) A methylaluminum chloride synthesized from aluminum and methylene chloride is brought into contact with sodium or magnesium, followed by reduction to afford trimethylaluminum (sesquichloride process).

(2) Aluminum is activated with an alkylaluminum and hydrogen. Ethylene is reacted to the resulting activated aluminum to obtain triethylaluminum, and by a substitution reaction, trimethylaluminum is then afforded (direct process).

(3) A mixture of aluminum, isobutylene and hydrogen is activated and reacted with a catalyst to obtain triisobutylaluminum. By a substitution reaction with ethylene, triethylaluminum is obtained, followed by a substitution reaction with methyl chloride to afford trimethylaluminum (isobutylene substitution process)

As the above processes use aluminum and an alkali metal or aluminum, it is considered that impurities such as silicon, iron, zinc, magnesium and sulfur are readily included in trimethylaluminum.

These impurities are considered to change into various compounds in the production steps. In particular, silicon, zinc and sulfur are considered to change into substances that readily include in organometallic compounds having one or more methyl groups, for example, trimethylaluminum and organometallic compounds available from trimethylaluminum as a raw material such as trimethylgallium and trimethylindium.

More specifically, in the case of organosilicon compounds, they include compounds represented by $Si(CH_3)_x(C_2H_5)_yCl_{4-x-y}$ and $Si(OCH_3)_x(C_2H_5)_yCl_{4-x-y}$ (x=0 to 4, y=0 to 4) such as tetramethylsilane, trimethylmethoxysilane, trimethylchlorosilane, silicon tetrachloride, and triethylmethylsilane. Alkylaluminum oxides and metal compounds are considered to include $(CH_3)_2AlOCH_3$ and $(CH_3)Al(OH)$, and $Zn(CH_3)_2$, $SCl_2$ and $S_2Cl_2$, although they are not limited thereto.

Further, the contents of the impurities are in the order of ppm or ppb. Such extremely low contents have made it difficult to establish their removal processes.

For the high purification of such crude trimethylaluminum, there have heretofore been reported adduct purification processes (JP-B 5-35154), processes involving distillation in contact with metallic sodium or metallic potassium (JP-A 62-132888), processes for purifying liquid organometallic compounds by cooling and solidifying them (JP-A 8-12678), and processes involving mixing of an organometallic compound containing one or more halogen and/or hydrogen atoms with an alkali halide and a subsequent heat treatment (JP-A 7-224071).

However, the adduct purification processes are accompanied by many drawbacks in that, as they require the addition of a solvent and the chemical for the treatment to trimethylaluminum to be purifyed, the purity of the solvent and chemical need to be made very high before its addition, the recovery rate of trimethylaluminum is low, the solvent and chemical have to be treated after use, the chemical is costly, and the operation is cumbersome.

The processes involving distillation in contact with metallic sodium or metallic potassium can separate organosilicon components to some extent, but the removal rate of organosilicon components is insufficient for compound semiconductors, especially for applications which require high purity.

The processes involving the cooling and solidification of organometallic compounds also have problems in that the removal rate of organosilicon components or alkylaluminum oxides from trimethylaluminum is not only unstable but also insufficient to obtain satisfactory results, require complex facilities for industrial practice, and also require cumbersome operations.

The processes involving mixing of an organometallic compound containing one or more halogen and/or hydrogen atoms with an alkali halide and a subsequent heat treatment to remove alkylaluminum oxides are also accompanied by problems in that their effect is limited to alkylaluminum oxides and moreover, their removal effect is insufficient.

SUMMARY OF THE INVENTION

It is an object of the present invention to provide high-purity trimethylaluminum in which the concentrations of impurities such as organosilicon components, chlorine components, hydrocarbon components, alkylaluminum oxides and metal compounds are lowered to extremity by an industrially easy process and at low cost and also to provide a purification method for stably obtaining the high-purity trimethylaluminum.

The present inventors have proceeded with an extensive investigation to achieve the above-described objects. As a result, it has been found that upon removing impurities from trimethylaluminum by distillation and evaporation, distillation with high-purity metallic sodium dissolved in trimethylaluminum makes it possible to effectively remove the impurities to afford high-purity trimethylaluminum by an industrially economical and easy process.

In one aspect of the present invention, there is thus provided a high-purity trimethylaluminum having the following impurity contents: organosilicon components $\leq 0.5$ ppm, chlorine components $\leq 20$ ppm, hydrocarbon components $\leq 1,000$ ppm, Ca $\leq 0.05$ ppm, Fe $\leq 0.05$ ppm, Mg $\leq 0.05$ ppm, Na $\leq 0.05$ ppm, Si (Si components other than the organosilicon components) $\leq 0.07$ ppm, Zn $\leq 0.05$ ppm, and S $\leq 0.05$ ppm. Preferably, a content of alkylaluminum oxides may not be higher than 20 ppm.

In another aspect of the present invention, there is also provided a method of purifying a crude trimethylaluminum comprising removing impurities from the crude trimethylaluminum through distillation and evaporation to afford the above-described high-purity trimethylaluminum. Preferably, metallic sodium substantially free of impurities may be added to the crude trimethylaluminum or to a solution of the crude trimethylaluminum and a solvent having a boiling point higher by at least 10° C. than trimethylaluminum to dissolve the metallic sodium, and then, the resulting solution may be distilled.

According to the method of the present invention, high-purity trimethylaluminum can be obtained economically with industrial ease. An epitaxial growth of the highly-purified trimethylaluminum can obtain a material for high-performance compound semiconductors. Further, the distillation residue can also be used as a catalyst for the production of a polyolefin having a relatively high purity, and owing to this industrial utility, the process of the present invention can also make up for its cost aspect.

DETAILED DESCRIPTION OF THE PREFERRED EMBODIMENTS

In the present invention, crude trimethylaluminum to be purifyed can be trimethylaluminum obtained by any one of the above-mentioned production processes (1) to (3), and no limitation is imposed on its production process. In particular, however, the sesquichloride process is preferred because no ethyl-containing component is contained in the organosilicon compounds and the separation of the organosilicon compounds in a subsequent step can be facilitated, although the purification process is not limited to the sesquichloride process.

In the crude trimethylaluminum produced by any one of the above-described processes (1) ro (3) and to be purified contains as impurities organosilicon compounds, alkylaluminum oxides, chlorine components and metal compounds originated from its raw material or operations, and hydrocarbon components originated from a solvent and decomposition products thereof in the order of from several % to ppm or ppb.

It is considered that the silicon components are converted into organosilicon compounds through chlorination or alkylation during reaction steps as mentioned above, the alkylaluminum oxides liberate alkoxy groups, hydroxyl groups and the like, and the remaining metal compounds are mostly converted into chlorides and include those to be methylated.

As the solvent, a high boiling-point hydrocarbon solvent is preferably used. This high boiling-point hydrocarbon solvent is often observed to undergo a phenomenon that in the reaction steps, a portion of the high boiling-point hydrocarbon solvent is decomposed or changed into low boiling-point hydrocarbons, which are then taken into trimethylaluminum.

Organosilicon compounds, hydrocarbon compounds and oxygen compounds, therefore, unavoidably include in the crude trimethylaluminum produced by the above-described synthesis process. Therefore, it is necessary to purify the crude trimethylaluminum in order to obtain high-purity trimethylaluminum.

More specifically, crude trimethylaluminum to be purified generally contains organosilicon components at 10 to 200 ppm, chlorine components at 50 to 100 ppm, hydrocarbon components (for example, as expressed in terms of hexane) at 5,000 to 10,000 ppm. Further, alkylaluminum oxides may also be contained at 50 to 200 ppm. It is to be noted that the term "the content or concentration of organosilicon components" as used herein means the content or concentration of Si in the above-described organosilicon compounds as impurities.

The purification method of the present invention for crude trimethylaluminum removes the above-mentioned impurities by distillation and evaporation. In this case, it is preferred to remove the impurities from the crude trimethylaluminum by adding metallic sodium, which is substantially free of impurities (specifically, a purity of 99.9% or higher), to the crude trimethylaluminum or a solution of the crude trimethylaluminum and a solvent having a boiling point higher by at least 10° C. than trimethylaluminum, for example, a compound represented by the below-described formula RnAr to dissolve the metallic sodium, and then, distilling the resulting solution.

$$R_nAr$$

wherein R represents a hydrogen atom, a methyl group, a substituted or unsubstituted aromatic hydrocarbon group having 6 to 16 carbon atoms, or an electrophilic substituent group, Ar represents a substituted or unsubstituted aromatic hydrocarbon group having 6 to 16 carbon atoms, n is an integer of from 1 to 14, and when n is an integer of 2 or greater, the plural Rs may be the same or different, with a proviso that n stands for 2 to 6 when Ar represents an aromatic hydrocarbon group having 6 carbon atoms and all Rs represent methyl groups.

Examples of the compound represented by $R_nAr$ include xylene, mesitylene, tetramethylbenzene, methylnaphthalene, dimethylnaphthalene, trimethylnaphthalene, dimethylanthracene, chlorotoluene, phenyltoluene, phenylnaphthalene, phenylanthracene, chlorobenzene, dichlorobenzene, trichlorobenzene, chloronaphthalene, dichloronaphthalene, fluorobenzene, difluorobenzene, trifluorobenzene, hexafluorobenzene, benzotrifluoride, perfluoronaphthalene, bromobenzene, dibromobenzene, tribromobenzene, nitrobenzene, benzonitrile, acetylbenzene, acetylnaphthalene, acetylanthracene, dimethylaminobenzene, aniline, and methoxynaphthalene. Particularly preferred are xylene, mesitylene, methylnaphthalene, chlorobenzene, dichlorobenzene, chlorotoluene, fluorobenzene, benzotrifluoride, and phenyltoluene.

Specifically, the purification method of crude trimethylaluminum can be conducted as will be described hereinafter. Firstly, fully-washed and dried facilities are provided. A still can preferably be provided with an agitator capable for producing an agitating force and shearing force to some extents, because metallic sodium is to be charged subsequently. Fittings and connections can preferably those capable of withstanding pressures of from high vacuum to 1.1 MPa.

Upon charging crude trimethylaluminum into the still, it is necessary to sufficiently purge the interior of the still with a high-purity inert gas (preferably at least 4 N, more preferably 6 N or so). Preferably, oxygen components are completely driven out of the system by using a vacuum pump and a heating means.

Next, metallic sodium is charged in a liquid form into the still from a container, which contains substantially no oxygen, while dissolving it in the crude trimethylaluminum. As the metallic sodium, pure metallic sodium making use of no solvent is preferred. Hydrocarbons such as liquid paraffin are not preferred not only for their low purity but also for their susceptibility to decomposition. Pure metallic sodium, which is substantially free of impurities, is then charged into the still while stirring under a high-purity inert gas such as nitrogen, helium or argon. If the amount of the high-purity sodium is unduly small relative to the amount of the crude trimethylaluminum to be purified, the effects of the high-purity sodium are reduced. Accordingly, the greater the amount of the high-purity sodium, the better. In the high-purity sodium, however, silicon, sulfur, calcium and oxygen components are also contained. To avoid the inclusion of such impurities into a distillate fraction in the subsequent purification, it is industrially preferred to charge 10 parts by weight or less, more preferably 2 to 5 parts by weight, of high-purity sodium per 100 parts by weight of crude trimethylaluminum.

To improve the separation performance, it is preferred to arrange as many equivalent trays as possible in a packed column. In this case, a height which can achieve a minimum holdup and is industrially advantageous is selected. To bring about sufficient separation/purification effects, a packed column with 10 trays or more but not greater than 30 trays is preferred. Concerning a condenser, a structure which can achieve a minimum holdup and can substantially eliminate liquid holding is also preferred.

A cut rate is the most important factor for stably obtaining high-purity trimethylaluminum.

The recovery rate of a main fraction is usually 70% or lower, with 50% or lower being preferred. The residue so discarded is used as a catalyst for the production of a polyolefin, and owing to this industrial utility, the process of the present invention can also make up for its cost aspect. This distillation purification can be repeated several times as needed, thereby making it possible to stably obtain high-purity trimethylaluminum.

By the above-described purification method, high-purity trimethylaluminum can be obtained with the following impurity contents: organosilicon components ≦0.5 ppm, preferably ≦0.1 ppm, chlorine components ≦20 ppm, preferably ≦10 ppm, hydrocarbon components ≦1,000 ppm, preferably ≦500 ppm, Ca≦0.05 ppm, Fe≦0.05 ppm, Mg≦0.05 ppm, Na≦0.05 ppm, Si (Si components other the organosilicon components)≦0.07 ppm, Zn≦0.05 ppm, and S≦0.05 ppm. It is also possible to obtain high-purity trimethylaluminum having a content of alkylaluminum oxides not higher than 20 ppm. Further, the contents of other metals, i.e., Cd, Cr, Cu, Mn, Ni, Sn, Ti and Zr can each preferably be not higher than 0.05 ppm.

EXAMPLES

Examples and Comparative Examples of the invention are given below by way of illustration and not by way of limitation. It is to be noted that the concentration of organosilicon components in the organometallic compounds of the following Examples was determined based on the quantitation by inductively-coupled plasma emission spectrometry subsequent to their extraction in a hydrocarbon solvent.

Example 1

After an SUS-made still equipped with an agitator and a packed column equivalent to 25 trays was thoroughly washed and then purged with helium, crude trimethylaluminum (100 parts by weight) was charged. Under environmental pressure, commercially-available, metallic sodium (5 parts by weight) was then charged into the still and was dissolved in the crude trimethylaluminum.

Subsequently, total reflux was conducted for 2 hours. During that time, the temperature of a condenser was controlled lower by 30° C. than the top temperature and, while introducing a high-purity inert gas at an appropriate flow rate into the condenser to avoid residence of low boiling-point impurities, the low boiling-point impurities were allowed to concentrate in the top. Thereafter, the distillation was conducted at a reflux ratio R=40 so that 40% of an initial distillate was discarded. The distillation was then continued at a reflux ratio of 15 to discard 45% of the main distillate. The bottom was transferred into a container provided separately, and was recovered by simple distillation. Analitical results of the main distillate are shown in Table 1.

TABLE 1

|  |  | Before purification (ppm) | After purification (ppm) |
| --- | --- | --- | --- |
| Organosilicon components | | 24.5 | 0.06 |
| Alkylaluminum oxides | | 130 | 15 |
| Hydrocarbon components | | 5,500 | 300 |
| Chlorine components (free) | | 50 | ≦10 |
| Metal elements | Ca | 0.08 | ≦0.05 |
| | Fe | 0.15 | ≦0.05 |
| | Mg | 0.07 | ≦0.05 |
| | Na | 0.13 | ≦0.05 |
| | Si | 0.07 | ≦0.05 |
| | Zn | 0.08 | ≦0.05 |
| | S | 0.15 | ≦0.05 |

Example 2

In a similar manner as in Example 1, crude trimethylaluminum of a different batch was purified twice, and as a result of measurement of the concentration of organosilicon components in trimethylaluminum (main distillate, 35%), the concentration was found to be 0.1 ppm. Analysis results of the main distillate are shown in Table 2.

TABLE 2

|  | Before purification (ppm) | After purification (ppm) |
| --- | --- | --- |
| Organosilicon components | 11.3 | 0.10 |
| Alkylaluminum oxides | 200 | ≦10 |
| Hydrocarbon components | 8,500 | ≦100 |
| Chlorine components (free) | 100 | ≦10 |
| Metal elements     Ca | 0.06 | ≦0.05 |
| Fe | 0.08 | ≦0.05 |
| Mg | 0.05 | ≦0.05 |
| Na | 0.20 | ≦0.05 |
| Si | 0.07 | ≦0.05 |
| Zn | 0.07 | ≦0.05 |
| S | 0.20 | ≦0.05 |

Comparative Example 1

In crude trimethylaluminum (100 parts by weight) of a similar batch as in Example 1, commercially-available metallic sodium (20 parts by weight) which had been treated with liquid paraffin was mixed. An initial distillate (20%) was discarded, and trimethylaluminum (main distillate, 60%) was obtained. Analysis results of the main distillate are shown in Table 3. It was impossible to remove organosilicon components to an extent sufficient for use in the production of high-function compound semiconductor materials.

TABLE 3

|  | Before purification (ppm) | After purification (ppm) |
| --- | --- | --- |
| Organosilicon components | 24.5 | 1.5 |
| Alkylaluminum oxides | 130 | 60 |
| Hydrocarbon components | 6,000 | 700 |
| Chlorine components (free) | 50 | ≦10 |
| Metal elements     Ca | 0.08 | ≦0.05 |
| Fe | 0.15 | ≦0.05 |
| Mg | 0.07 | ≦0.05 |
| Na | 0.13 | ≦0.05 |
| Si | 0.07 | ≦0.05 |
| Zn | 0.08 | ≦0.07 |
| S | 0.07 | ≦0.06 |

The invention claimed is:

1. A high-purity trimethylaluminum having the following impurity contents:

organosilicon components≦0.1 ppm, chlorine components≦20 ppm, hydrocarbon components≦1,000 ppm, Ca≦0.05 ppm, Fe≦0.05 ppm, Mg≦0.05 ppm, Na≦0.05 ppm, Si (Si components other than said organosilicon components)≦0.07 ppm, Zn≦0.05 ppm, and S≦0.05 ppm.

2. The high-purity trimethylaluminum according to claim 1, wherein a content of alkylaluminum oxides is not higher than 20 ppm.

3. A method of purifying a crude trimethylaluminum comprising removing impurities from the crude trimethylaluminum to be purified through distillation and evaporation to afford high-purity trimethylaluminum as defined in claim 1.

4. A process according to claim 3, wherein metallic sodium substantially free of impurities is added to the crude trimethylaluminum to dissolve the metallic sodium therein and the resulting solution is distilled.

5. A process according to claim 3, wherein metallic sodium substantially free of impurities is added to a solution of the crude trimethylaluminum and a solvent having a boiling point higher by at least 10° C. than trimethylaluminum to dissolve the metallic sodium therein, and the resulting solution is distilled.

\* \* \* \* \*